(12) United States Patent
Ganchi

(10) Patent No.: US 7,138,131 B2
(45) Date of Patent: Nov. 21, 2006

(54) METHOD FOR HAND REJUVENATION

(76) Inventor: Parham A. Ganchi, 59 Laurel Ave., West Orange, NJ (US) 07052

( * ) Notice: Subject to any disclaimer, the term of this patent is extended or adjusted under 35 U.S.C. 154(b) by 0 days.

(21) Appl. No.: 11/106,809

(22) Filed: Apr. 15, 2005

(65) Prior Publication Data

US 2006/0233856 A1    Oct. 19, 2006

(51) Int. Cl.
*A61F 2/00* (2006.01)
(52) U.S. Cl. ..................................... 424/423
(58) Field of Classification Search ................ 424/423; 623/11; 514/2
See application file for complete search history.

(56) References Cited

OTHER PUBLICATIONS

Lattari V et al. "The use of a permanent dermal allograft in full-thickness burns of the hand and foot: a report of three cases". J. Burn Care Rehabil., 1997, 18(2): 147-155. entire document.*

Lifecell Corporation: The product "Alloderm" and also see at the web http://www.lifecell.com. Implanting Alloderm in the OR, Grafting with Alloderm in the OR, pp. 1-8.*

Facial Plastic Surgery Network, at the web http://www.facialplasticsurgery.net. Wrinkles: smoothing the hands of time, Web site last updated Mar. 11, 2003, pp. 1-4.*

* cited by examiner

*Primary Examiner*—Sandra E. Saucier
*Assistant Examiner*—Satyendra K. Singh
(74) *Attorney, Agent, or Firm*—Reza Mollaaghababa; Nutter McClennen & Fish LLP

(57) ABSTRACT

The present invention provides a method of rejuvenating human skin by implanting a sheet formed of a pliable biocompatible material beneath the skin surface so as to generate a substantially smooth layer that augments a thickness of the skin portion. The biocompatible sheet has preferably a thickness sufficient for substantially camouflaging the underlying anatomical structure (e.g., veins and tendons).

5 Claims, 3 Drawing Sheets

GENERATE ONE OR MORE INCISIONS AT SELECTED POSITIONS OF A PATIENT'S HAND TO PROVIDE AN OPENING FOR ACCESSING THE DORSUM — 12

INSERT A PLIABLE BIOCOMPATIBLE SHEET THROUGH THE OPENING TO BE PLACED UNDER A PORTION OF THE HAND SKIN TO HIDE UNDERLYING ANATOMICAL STRUCTURES — 18

METHOD FOR HAND REJUVENATION

BACKGROUND OF THE INVENTION

The present invention relates generally to methods of enhancing the appearance of a patient's skin, and more particularly to methods for cosmetic rejuvenation of a patient's hand.

A variety of cosmetic surgical procedures are routinely performed on the face and body. Some examples of these procedures include facial rejuvenation, body contouring and nasal surgery. Further, a number of surgical techniques are known for reducing signs of aging exhibited by a person's hands. In one such technique, a quantity of lipid tissue can be injected under the skin surface of an aging hand to enhance its appearance. Such a procedure can, however, have a number of shortcomings. The injected lipid can resorb over time, thereby reducing the effectiveness of the treatment. Further, the outcome of such a procedure can be somewhat unpredictable.

Hence, there is a need for improved techniques for enhancing the appearance of aging in an individual's hands.

SUMMARY OF THE INVENTION

The present invention generally provides surgical methods for rejuvenating the appearance of human skin. Such methods can be employed to enhance the appearance of the skin of different body portions, and can be particularly efficacious when applied to the hand.

In one aspect, a method of rejuvenating human skin is disclosed that includes implanting a sheet formed of a biocompatible pliable material beneath the surface of a skin portion so as to generate a substantially smooth layer that augments a thickness of that skin portion. This augmentation of the skin thickness can provide the skin with a more supple appearance. Further, the pliable sheet can be selected so as to substantially disguise underlying anatomical structures, such as blood vessels and tendons, that can give an appearance of aging, when visible through the skin surface.

In a related aspect, the pliable biocompatible sheet can be formed of processed cadaveric dermis, silicone, a lattice of acellular dermis or polytetrafluoroethylene (PTFE), or any other suitable biocompatible material that is sufficiently flexible for implantation below the skin. In preferred embodiments, the thickness of the sheet can be chosen to provide effective camouflage of underlying anatomical structures. For example, the sheet's thickness can be in a range of about 0.1 millimeter (mm) to about 2 mm (e.g., in a range of about 0.15 mm to about 2 mm). In some embodiments, the sheet can have a multi-layer structure.

In another aspect, the present invention provides a method of enhancing appearance of a human hand that includes generating an incision in proximity of the wrist, and lifting a portion of the hand skin to form a subcutaneous pocket. Subsequently, a sheet formed of a pliable biocompatible material is inserted into the pocket, and is flattened to form a substantially smooth subsurface layer. The incision can then be closed. The subsurface layer can at least partially disguise the underlying anatomical structures to rejuvenate the appearance of the skin.

In further aspects, a method of rejuvenating a patient's hand is disclosed that includes implanting one or more pliable sheets formed of a biocompatible material below a portion of the hand's skin surface in a substantially flattened configuration to generate a subsurface buffering layer capable of disguising underlying irregularities. The implantation step can include forming an incision in a selected location of the patient's hand, inserting the pliable biocompatible sheet through the incision within a subcutaneous pocket formed under the skin, and securing the sheet in place in a flattened configuration.

Further understanding of the invention can be obtained by reference to the following detailed description in conjunction with the associated drawings, which are described briefly below.

BRIEF DESCRIPTION OF THE DRAWINGS

FIG. 1 is a flow chart depicting various steps in an exemplary embodiment of a method according to the teachings of the invention for rejuvenating the appearance of a subject's hand, FIG. 2A schematically illustrates an incision made in a patient's dorsal wrist crease in one step of the method described in the flow chart of FIG. 1, through which a biocompatible sheet can be inserted beneath the skin, FIG. 2B schematically illustrates disposition and anchoring of the biocompatible sheet shown in FIG. 2A underneath the patient's skin, and FIG. 3 schematically illustrates a pliable biocompatible sheet suitable for use in the practice of the invention.

DETAILED DESCRIPTION

The present invention provides methods for enhancing the appearance of a portion of the skin by implanting a pliable sheet formed of a biocompatible material under the skin. In many embodiments, the sheet is formed of processed cadaveric dermis, such as that marketed by LifeCell Corporation of Branchburg, N.J., U.S.A. under the trade designation Alloderm™. In the embodiment that follows, the teachings of the invention are illustrated with respect to rejuvenating the appearance of a person's hands. It should, however, be understood that the teachings of the invention can be applied to other anatomical parts, as discussed further below.

Figure 2A:
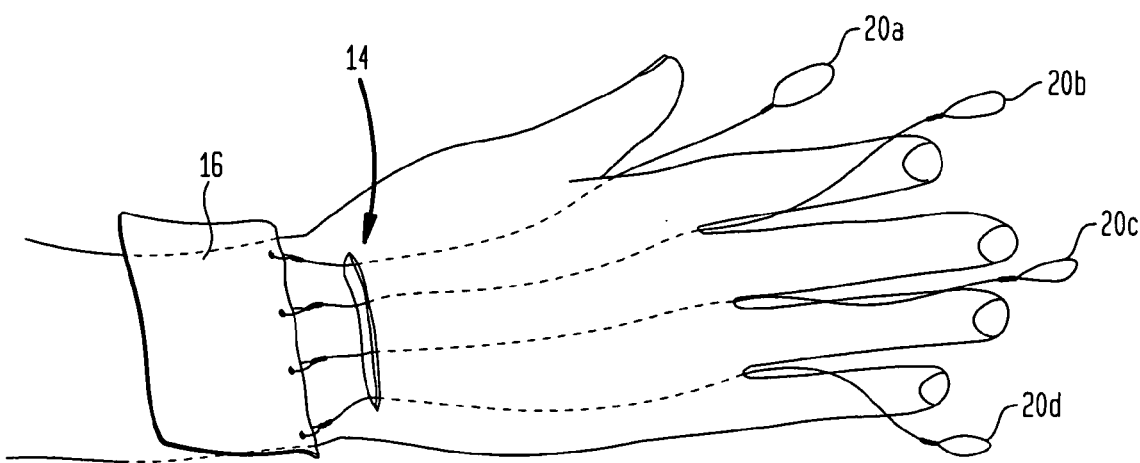
Figure 2B:
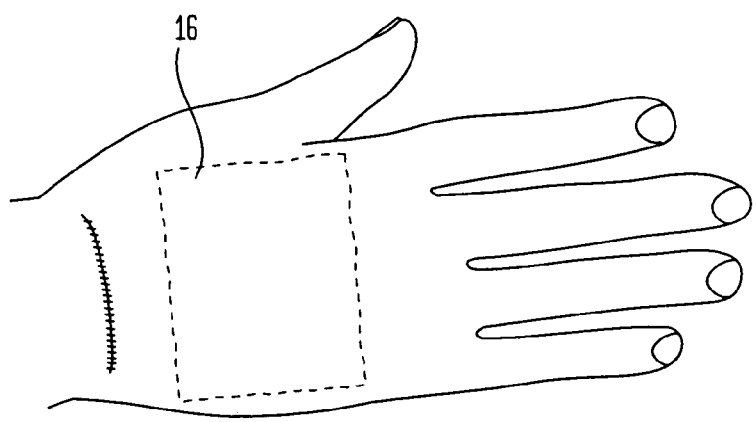

With reference to a flow chart 10 of FIG. 1, as well as FIGS. 2A and 2B, in one exemplary method according to the teachings of the invention for rejuvenating the appearance of a patient's hand, in an initial step 12, one or more incisions are made at selected positions of a patient's hand that are cosmetically advantageous. For example, in this embodiment, as shown schematically in FIG. 2A, one incision 14 can be made at the patient's dorsal wrist crease to provide opening for accessing the dorsum. The skin can be lifted to generate a subcutaneous pocket in which a pliable biocompatible sheet 16 can be inserted, as discussed below. It should be understood that the size of the incision can be selected at least partly based on the technique that will be utilized for placement of the sheet, as well as consideration relating to cosmesis.

Referring again to the flow chart 10, in a subsequent step 18, the biocompatible sheet 16 is inserted through the incision to be placed under the patient's hand skin, as shown schematically in FIG. 2B. A number of "pulling" or "pushing" techniques can be employed for placing the sheet beneath the skin. The biocompatible sheet 16, which can be initially in a rolled-up configuration, can be pushed, for example, via an instrument (e.g., a forcep), through the opening under the patient's skin. Once inserted, the sheet can be unraveled by employing, for example, a blunt instrument (e.g., a small forcep when incision is small) or even the surgeon's finger (e.g., when the incision is sufficiently large), to provide a substantially smooth and uniform layer that can camouflage the underlying anatomical structures.

Alternatively, as shown schematically FIGS. 2A–2B, in addition to the dorsal incision 14, a plurality of distal access points 20a, 20b, 20c and 20d (collectively referred to as access points 20) can be utilized for inserting a plurality of sutures that can be coupled to the rolled-up sheet to pull the sheet into a selected space beneath the skin. These distal incisions are preferably located so as to allow a surgeon not only to pull the sheet into the subcutaneous space but also to initiate unraveling the sheet in a substantially uniform manner. Additional smoothing of the unraveled sheet can be achieved via an instrument or the surgeon's finger through the dorsal incision. This "pulling" technique can be particularly advantageous in that it provides a more efficient way of initially placing the sheet into a desired space beneath the skin as well as more control in fixating it at the distal points of the subcutaneous pocket. Moreover, the distal stitches can remain in place for a selected period after surgery to continue anchoring the sheet in its proper position even when the patient moves his/her hand. They can be removed when the surgeon determines that sufficient healing has been achieved and the risk associated with the sheet's migration is minimal. In some embodiments, in addition to the above distal stitches, a plurality of side stitches (not shown) can be utilized to further enhance anchoring of the sheet in its proper position under the subject's skin.

The biocompatible sheet 16 has a sufficient thickness, for example, a thickness in a range of about 0.1 mm to about 2 mm, and more preferably in a range of 0.15 mm to about 2 mm, so as to provide a desired cosmetic effect. For example, it may be utilized to substantially hide/camouflage underlying anatomical features, such as veins and tendons, so as to provide a more youthful appearance of the skin. It should be understood that the thickness of the sheet can be chosen based on the desired effect as well as the type of biocompatible material from which the sheet is formed. For example, when the sheet is formed of a more pliable material, for example, Alloderm™, an effective thickness may be larger than when it is formed of a less pliable material, for example, Gortex (PTFE).

Figure 3:
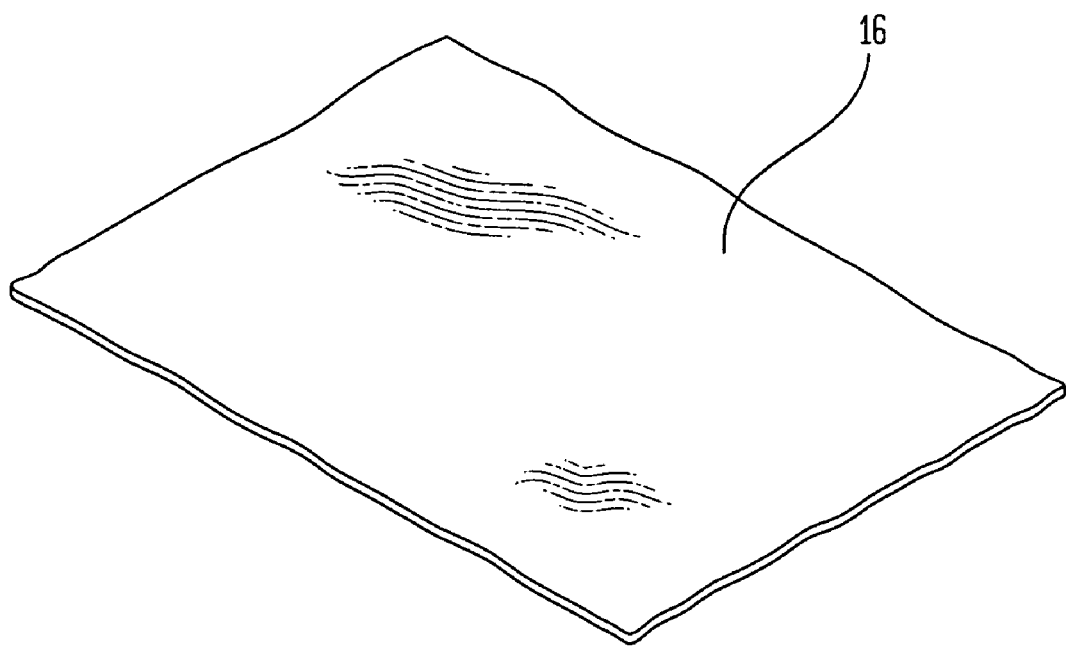

In many embodiments of the invention, the biocompatible sheet 16, shown schematically in FIG. 3, is formed of cadaveric human skin allograft (i.e., human dermis devoid of cellular components) to provide a smooth subcutaneous layer for hiding the underlying anatomical structures, thereby imparting a more youthful appearance to the hand. In other embodiments, the sheet 16 can be formed of polytetrafluoroethylene (PTFE) polymer or silicone. In fact, the sheet can be formed of any suitable bicomapatible material that is sufficiently flexible for inserting under the skin and is suitable for long-term implantation in a human.

In the above illustrative embodiment, a single sheet was utilized. However, in other embodiments, more than one sheet can be inserted under a patient's skin so as to provide a desired cosmetic effect. For example, a plurality of sheets can be placed side-by-side to cover an area of interest or they can be stacked one over another to enhance the effective thickness.

Although the above description was primarily directed to rejuvenation of the appearance of a human hand, the methods described above can also be utilized for imparting a more youthful appearance to other anatomical parts. For example, a biocompatible sheet can be inserted in a subcutaneous pocket generated in a patient's foot in a manner similar to that discussed above to provide a smooth layer suitable for camouflaging the underlying anatomical structures.

Those having ordinary skill in the art will appreciate that various changes can be made to the above embodiments without departing from the scope of the invention.

What is claimed is:

1. A cosmetic method of rejuvenating a patient's hand, comprising implanting at least one pliable sheet formed of a biocompatible material below a portion of the hand's skin in a substantially flattened configuration to generate a subsurface buffering layer capable of disguising underlying anatomical structures, wherein the step of implanting further comprises forming an incision in a selected location of the patient's hand, inserting the pliable biocompatible sheet through the incision within a subcutaneous pocket formed under a portion of the hand's skin, and securing the implanted sheet in a flattened configuration.

2. The method of claim 1, further comprising selecting said sheet to be formed of any one of cadaveric dermis, silicone or polytetrafluoroethylene.

3. The method of claim 2, further comprising selecting said sheet to have a thickness in a range of about 0.15 mm to about 2 mm.

4. The method of claim 1, further comprising said sheet to be formed of a porous material.

5. The method of claim 1, wherein the said location of the patient's hand comprises the wrist.

* * * * *